United States Patent [19]

Menke

[11] 4,227,976

[45] Oct. 14, 1980

[54] MAGNESIUM ANODIZE BATH CONTROL

[75] Inventor: Joseph T. Menke, Davenport, Iowa

[73] Assignee: The United States of America as represented by the Secretary of the Army, Washington, D.C.

[21] Appl. No.: 25,632

[22] Filed: Mar. 30, 1979

[51] Int. Cl.³ .................. G01N 27/42; G01N 31/16; C25D 11/30
[52] U.S. Cl. .................. 204/56 M; 23/230 R; 204/1 T
[58] Field of Search .................. 23/230 R; 204/56 M, 204/1 M

[56] References Cited

FOREIGN PATENT DOCUMENTS 331310  4/1972  U.S.S.R. .................. 23/230 R

OTHER PUBLICATIONS

Dow Chemical Co. Instruction Form No. 147-39-70, exact pub. date unknown.
MIL-M-45202B, date unknown.
Ari Ivaska, Talanta, vol. 21, No. 11, pp. 1167-1173, (1974).

Primary Examiner—G. L. Kaplan
Attorney, Agent, or Firm—Nathan Edelberg; Robert P. Gibson; Robert O. Richardson

[57] ABSTRACT

An analytical method to determine and control the chemical composition and concentration of a magnesium anodizing solution consisting of three chemicals, sodium dichromate, ammonium bifluoride and phosphoric acid, such as in Chemical Treatment No. 17 of Dow Chemical Company, for example. Automatic pH titration is used to determine the amount of ammonium bifluoride ($NH_4HF_2$) and phosphoric acid ($H_3PO_4$) concentration at the same time and the concentration of sodium dichromate ($Na_2Cr_2O_7.2H_2O$) is determined separately by the thiosulfate titration technique.

1 Claim, 4 Drawing Figures

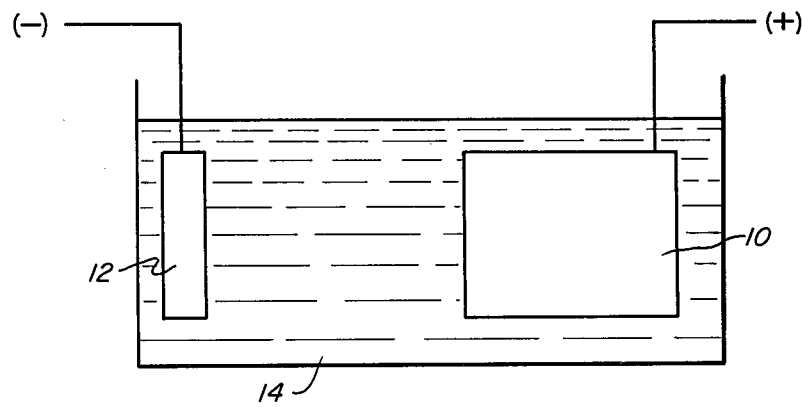
Fig__1__
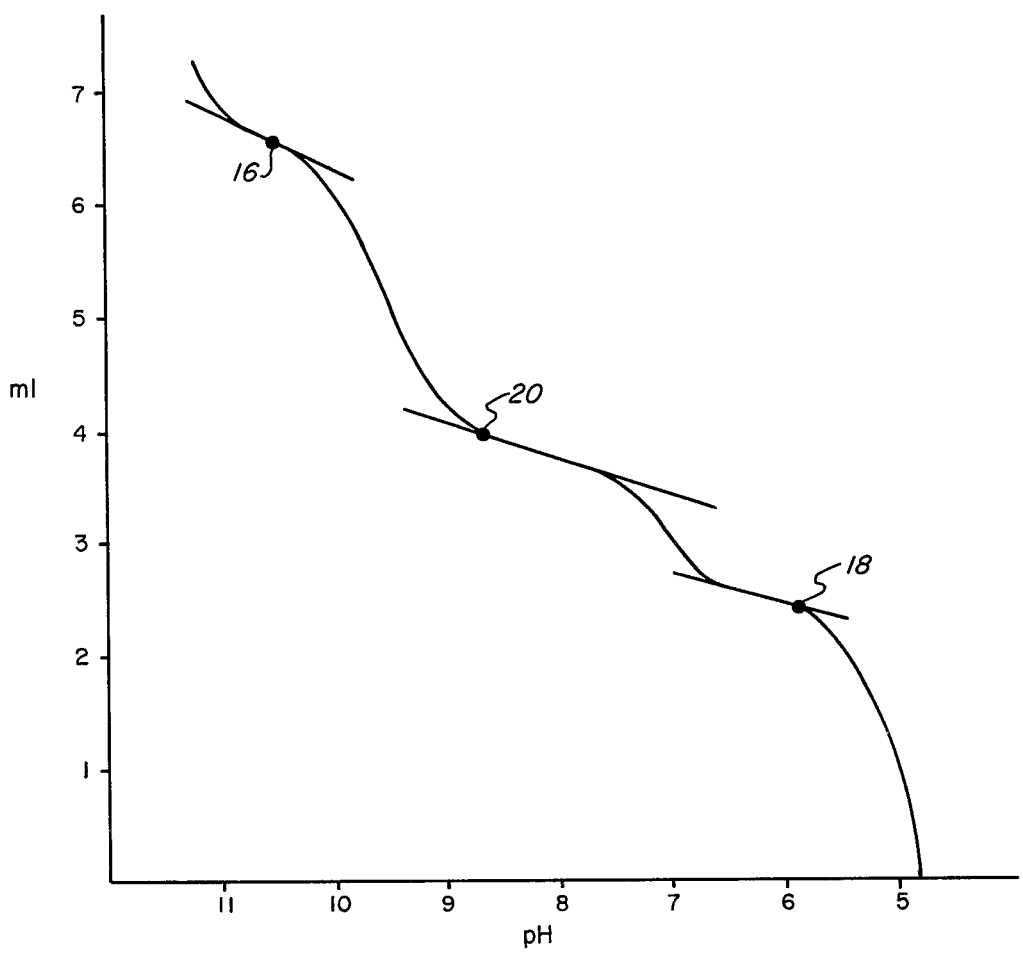
Fig__2__

MAGNESIUM ANODIZE BATH CONTROL

Government Rights

The invention described herein may be manufactured and/or used by or for the Government for governmental purposes without the payment of any royalty thereon.

BACKGROUND OF THE INVENTION

It is possible to determine the amount of acidity of a solution by adding a caustic solution to it in a sufficient amount to neutralize the solution. The greater the amount of caustic solution required, the greater was the acidity of the original solution. A lesser amount of caustic solution needed is an indication that the original solution was less acid. The degree of acid or alkaline content of a solution is expressed as a pH number. pH is the negative logarithm of the hydrogen ion activity in gram equivalents per liter. pH 7 is considered neutral with pH numbers smaller than 7 indicating acidity and pH numbers larger than 7 indicating alkalinity. Various formulae have been devised to indicate how much more acid or caustic ingredients need be added to give the sample solution a desired greater acidity or caustic strength.

The foregoing problem and its solution is more difficult and is compounded when the sample solution includes three ingredients whose original concentrations were known but which become used up at different unknown rates during operation. Such is the case of a bath solution used in anodizing magnesium.

Magnesium is a light structural material that corrodes under ordinary atmospheric conditions and thus must be coated to protect it from corrosion. A preferred coating process prior to painting of the magnesium is anodizing. Chemical Treatment No. 17 of Dow Chemical Company is a typical anodizing bath consisting of ammonium acid fluoride or ammonium bifluoride ($NH_4HF_2$), sodium dichromate ($Na_2Cr_2O_7.2H_2O$) and phosphoric acid ($H_3PO_4$). At this bath is used in the anodizing process, the proportionate amounts of these chemicals will vary as the ingredients are used up at different rates. With a resulting improperly mixed bath, the magnesium part doesn't have the adequate protective build-up that it should; it displays rejectionable colors and other processing problems which result in an unacceptable anodized part. For this reason it is important to maintain the proper mix of the anodizing solution.

Current analytical procedures for determining the content of a magnesium anodizing bath are set forth in a Dow Chemical Company Instruction Form No. 147-39-70 entitled, Product and Process Data—Magnesium—Chemical Treatment No. 17, which has been available since at least 1973. These procedures are also set forth in MIL-M-45202B. Briefly, chromate is reduced with excess ferrous sulfate. The excess ferrous iron is titrated with potassium dichromate. An alternate procedure for determining chromium is by adding hydrochloric acid (HCl) and potassium iodide (KI) to the sample to liberate free iodine. Iodine is titrated with sodium thiosulfate with a starch indicator. This is known as the thiosulfate method. Phosphorus is precipitated as ammonium phosphomolybdate, the precipitate is dissolved in an excess of standard base, and the excess base is titrated with standard acid to the phenolphthalein end point. Interference from fluorides is prevented by adding boric acid to form harmless fluoboric acid. The colored chromate ion is precipitated as silver chromate in an alkaline solution. The solution is filtered and the fluoride ion in the filtrate is determined by titration with thorium nitrate using alizarin sulfonate as an indicator.

Current analytical procedures involve complex precipitation techniques which are time consuming, requiring approximately twenty hours per analysis. The new control procedure of the present invention is reliable yet requires only one hour because the time required for fluoride and phosphorus analysis is greatly reduced.

SUMMARY OF THE PRESENT INVENTION

In accordance with the present invention a magnesium anodize bath control has been developed wherein an automatic pH titration, with sodium hydroxide, as the titrant, is used to determine the amount of ammonium bifluoride and phosphoric acid concentration at the same time. The sodium dichromate concentration is determined separately by the thiosulfate titration technique.

In practice a sample of the mixture is diluted, placed in a beaker and subjected to autotitration. While this is being done, a second titration is made to determine the chromium content. Using 1 normal sodium hydroxide (1.0 N NaOH) in an automatic titrator, a curve showing various end points may be obtained from a sample bath of known concentration. Form the curve it is possible to determine the amount of ammonium bifluoride ($NH_4HF_2$) present. Using the thiosulfate titration method, the amount of sodium dichromate ($Na_2Cr_2O_7.2H_2O$) can be determined and back calculated to the volume represented. This is necessary because the sodium dichromate and phosphoric acid overlap on the titration curve when sodium hydroxide is used as the titrant.

The concentration of the phosphoric acid can then be determined, knowing the total milliliters (ml) required for neutralization of the sodium dichromate and phosphoric acid and then subtracting the sodium dichromate volume calculated using the thiosulfate method. Knowing the concentrations of the various ingredients in the bath, appropriate additions to the bath can be determined to return the bath to its desired state.

BRIEF DESCRIPTION OF DRAWINGS

FIG. 1 is a schematic illustration of magnesium anodizing apparatus,

FIG. 2 is a graphic illustration of the titration curve of a known anodize solution.

DETAILED DESCRIPTION OF ILLUSTRATIVE EMBODIMENTS

Figure 3:
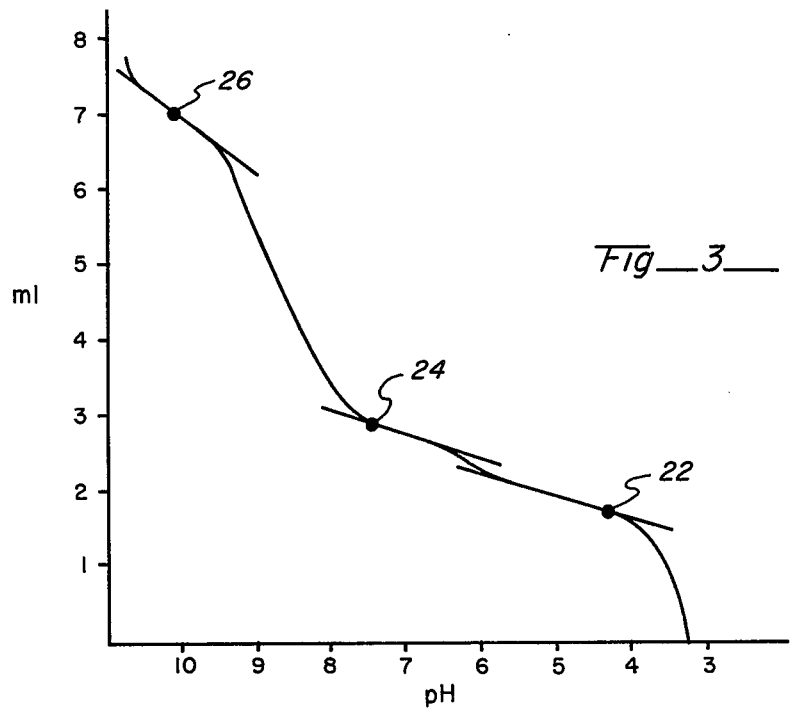
FIG. 3 is a graphic illustration of the titration curve of the anodize solution after use and in need of replenishment.

Reference is now made to FIG. 1 wherein is shown a magnesium part 10 to be anodized. It is connected as the anode to the positive terminal of a direct current source, not shown. An inert cathode 12, such as steel for example, is connected to the negative terminal. Both parts are placed in an anodizing bath 14. As the magnesium part 10 is thus anodized, the balance or ratio of the ingredients in the bath changes and some ingredients eventually become used up. When this occurs, subsequent parts are no longer anodized properly.

The anodizing bath preferably is Dow 17, made by the Dow Chemical Company. It consists of:

Ammonium bifluoride—300 g/l (40.2 oz/gal)
Sodium dichromate—100 g/l (13.4 oz/gal)
Phosphoric Acid (85%)—150 g/l (20.1 oz/gal).

A small deviation from these amounts is permissible.

Before using the anodizing bath a titration curve is made with an automatic titrator. Such a curve is shown in FIG. 2. The titrator progressively adds sodium hydroxide to a sample of the bath and the curve is a plot of the pH change with increase in the additive. Here the pH changes from 5 to 11 as the sodium hydroxide is increased to 7 milliliters. This curve represents the pH characteristics of the bath consisting of the three ingredients, ammonium bifluoride, phosphoric acid, and sodium dichromate. It is noted that this curve has three end points, the third one representing the end of the titration. This occurred at approximately pH 10.5. When a line is drawn tangent to the flat part of the curve and the midpoint located (point 16) it may be seen that the neutralization of the composite sample was 6.75 ml.

By process of titrating separate solutions of each of the ingredients it was found that the first end point 18 was the reaction of the ammonium bifluoride to titration, and that sodium dichromate and phosphoric acid could not be separated on the titration curve when using sodium hydroxide as the titrant. Hence, the second end point 20 represents the titration of the combination. The difference in volume of titrant added to reach end point 18 and to reach end point 20 is 1.65 ml, the amount necessary to neutralize the combination of sodium dichromate and phosphoric acid. The rest of the neutralizing additive reacted with the ammonium bifluoride. Hence, the volume of additive for ammonium bifluoride alone is 6.75 ml (at end point 16) minus the 1.65 ml required for the sodium dichromate and phosphoric acid combination. This is 5.10 required for ammonium bifluoride neutralization.

Using the thiosulfate titration method, a sodium dichromate analysis is made (the dichromate and phosphoric acid cannot be separated in the titration curve when sodium hydroxide is used as the titrant). This analysis is done by adding potassium iodide (KI) and concentrated hydrochloric acid (HCl) to the sample and titrating the liberated iodine with sodium thiosulfate (0.1 N $Na_2S_2O_3^6$) until the yellow color is almost gone. Several drops of starch indicator solution are then added and titration is continued with the thiosulfate until the purple starch-iodine color disappears. Knowing the chromium content (0.04975 g/ml) based on the thiosulfate titration, the number of ml of sodium hydroxide required to neutralize the sodium dichromate is determined by dividing the 0.04975 g/ml by the equivalent weight of sodium dichromate, which is 0.149 g. This calculation shows that 0.33 ml of sodium hydroxide is required to neutralize the sodium dichromate.

The strength of the phosphoric acid can then be determined by the difference between the total ml required for neutralization of the bath sample (6.75 ml) and the ml of titrant required for the ammonium bifluoride (5.10 ml) and sodium dichromate (0.33 ml).

Knowing the concentrations in ml of each of the ingredients in the sample, it is then possible to compute by weight, the ingredients in the bath. In the foregoing analysis it was determined that the amount of ammonium bifluoride was 292 g/l, the sodium dichromate was 99.5 g/l, and the phosphoric acid was 152 g/l. These compare favorably with the labeled compositions in the new bath.

Having used the method of this invention to establish the strengths of the ingredients of the Dow 17 Magnesium Anodize Bath when fresh and having verified them to be substantially as labeled, the procedure then may also be used to determine the unknown strengths of the ingredients after the bath has been used for some time. The titration curve of such a solution is shown in FIG. 3.

In FIG. 3 the difference between end points 22 and 24 is 1.2 ml of titrant sodium hydroxide. End point 26 requires 7 ml. Thus, the concentration of ammonium bifluoride is 7.0−1.2=5.8 ml or 5.8×57.0 (conversion factor)=330 g/l ammonium bifluoride. To get an end point from the thiosulfate titration, 56.9 ml of thiosulfate are required. Thus, 56.9×1.88 (conversion factor)=107 g/l, the concentration of sodium dichromate in the sample. 107 g/l of sodium dichromate÷298 (conversion factor)=0.36 ml of sodium hydroxide required to neutralize the sodium dichromate between end points 22, 24. Thus, 1.2−0.36=0.84 ml of sodium hydroxide is required to neutralize the phosphoric acid. The concentration of phosphoric acid in the bath, then, is 0.84×115 (conversion factor)=96 g/l of phosphoric acid. Upon comparison with the new bath concentrations, 300 g/l vs. 330 for ammonium bifluoride, 100 g/l vs. 107 for sodium dichromate, and 150 g/l vs. 96 for phosphoric acid, it can be seen that the phosphoric acid concentration is too low and needs replenishing. Once the concentrations of the various ingredients of the anodize bath are known, one skilled in the art can determine the amount of each additive that is necessary to bring them up to the desired strength.

Figure 4:
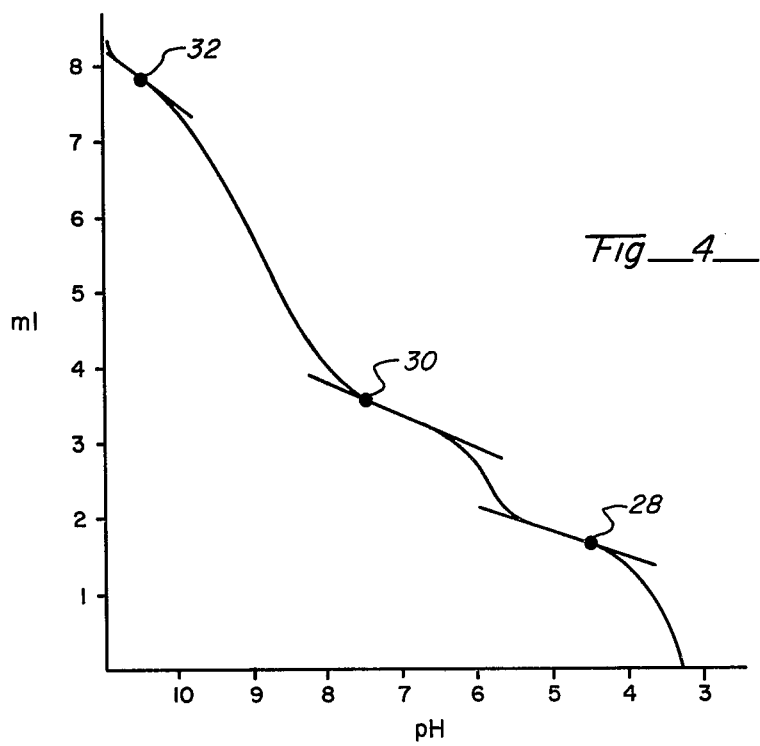
FIG. 4 is a graphic illustration of the anodize solution after proper additions have been made.

FIG. 4 shows the titration curve of Dow 17 bath solution after it has been used and then the ingredients were replenished. Here end point 32 is at 7.9 ml, the amount of sodium hydroxide needed to neutralize the bath. End point 30 requires 1.8 ml more titrant than end point 28, establishing 7.9−1.8=6.1 ml of titrant required to neutralize the ammonium bifluoride. This means that its concentration in the bath is 6.1×57.0 (conversion factor)=348 g/l, a permissible overstrength compared to the 300 g/l in the new bath. 50.0×1.88 (conversion factor)=94 g/l concentration of sodium dichromate, within tolerance compared to the 100 g/l recommended. 94 g/l÷298 (conversion factor)=0.31 ml of titrant is required to neutralize the dichromate. Hence, 1.8−0.31 =1.49 ml required for the phosphoric acid in the sample. 1.49×115 (conversion factor)=172 g/l of phosphoric acid, compared to the 150 g/l in a new bath.

In summary, the invention consists of running titration curves of various combinations and selected ingredients forming a composite bath to identify the end points of various ingredients. Those ingredients having overlapping curves are then titrated with a different titrant to determine the concentration of one ingredient. This concentration subtracted from the composite concentration gives the concentration of the other ingredient. Having then found all the ingredients' concentrations, the additive amounts of each can then be calculated to bring each ingredient up to desired strength. For example, in FIG. 3, the sample had 96 g/l of phosphoric acid when 150 was desired. Thus, the difference times the volume of the bath (150−96×liters of bath volume) is the number of grams of phosphoric acid needed to restore the bath to operational strength.

While this method has been described with reference to the Dow 17 Magnesium Anodize Bath consisting of ammonium bifluoride, sodium dichromate and phosphoric acid as an example, obviously this technique for analyzing the concentrations of various ingredients in a composite mixture may be used in various combinations of mixtures and that modifications and alterations will occur to one skilled in the art. Such deviations from the illustrative example are to be considered as part of the present invention as set forth in the following claims.

The invention in its broader aspects is not limited to the specific combinations, improvements and instrumentalities described but departures may be made therefrom within the scope of the accompanying claims without departing from the principles of the invention and without sacrificing its chief advantages.

What is claimed is:

1. A method of controlling the concentration of ingredients in a magnesium anodize bath of ammonium bifluoride, sodium dichromate and phosphoric acid including the steps of:
   a. titrating dichromate, bifluoride and acid combinations to identify various end points on the titration curve and to observe the pH neutralization curve characteristics,
   b. titrating a bath sample with sodium hydroxide to determine the neutralization end point of the bath and the amount of ammonium bifluoride therein,
   c. observing from the titration curve derived from step b the combined amount of sodium dichromate and phosphoric acid in the bath sample,
   d. titrating another bath sample with thiosulfate to determine the amount of sodium dichromate in the bath and hence the amount of phosphoric acid, and
   e. thereafter adding desired additional amounts of each ingredient to make them of desired strength in said bath.

* * * * *